US012628820B2

(12) United States Patent
Menze et al.

(10) Patent No.: US 12,628,820 B2
(45) Date of Patent: May 19, 2026

(54) SYSTEMS AND METHODS FOR PRESERVATION OF CELLS

(71) Applicant: UNIVERSITY OF LOUISVILLE RESEARCH FOUNDATION, Inc., Louisville, KY (US)

(72) Inventors: Michael Menze, Louisville, KY (US); Jonathan Kopechek, Louisville, KY (US); Brett Janis, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 129 days.

(21) Appl. No.: 16/622,361

(22) PCT Filed: Jun. 14, 2018

(86) PCT No.: PCT/US2018/037444
§ 371 (c)(1),
(2) Date: Dec. 13, 2019

(87) PCT Pub. No.: WO2018/232058
PCT Pub. Date: Dec. 20, 2018

(65) Prior Publication Data
US 2020/0196596 A1 Jun. 25, 2020

Related U.S. Application Data

(60) Provisional application No. 62/519,638, filed on Jun. 14, 2017, provisional application No. 62/667,826, filed on May 7, 2018.

(51) Int. Cl.
| | |
|---|---|
| A01N 1/162 | (2025.01) |
| A01N 1/165 | (2025.01) |
| A61M 1/02 | (2006.01) |
| C12N 5/00 | (2006.01) |

(52) U.S. Cl.
CPC ............ *A01N 1/162* (2025.01); *A01N 1/165* (2025.01); *A61M 1/0272* (2013.01); *C12N 5/0068* (2013.01); *A61M 2202/0429* (2013.01); *A61M 2205/0244* (2013.01); *A61M 2205/058* (2013.01); *C12N 2500/34* (2013.01); *C12N 2502/115* (2013.01); *C12N 2521/10* (2013.01)

(58) Field of Classification Search
CPC .... A01N 1/0284; A01N 1/0289; A01N 1/162; A01N 1/165; A61M 1/0272; A61M 2202/0429; A61M 2205/0244; A61M 2205/058; C12N 5/0068; C12N 2500/34; C12N 2502/115; C12N 2521/10
See application file for complete search history.

(56) References Cited

U.S. PATENT DOCUMENTS

| | | | |
|---|---|---|---|
| 10,058,837 B2 * | 8/2018 | Borden | A61K 49/223 |
| 10,407,655 B2 * | 9/2019 | Hinojosa | B01L 3/50273 |
| 11,007,495 B2 * | 5/2021 | Stride | B01F 25/3141 |
| 11,299,698 B2 * | 4/2022 | Sharei | A61P 33/06 |
| 2005/0277107 A1 * | 12/2005 | Toner | A01N 1/02 435/2 |
| 2012/0328529 A1 * | 12/2012 | Lee | A61K 49/223 424/9.5 |
| 2013/0129635 A1 * | 5/2013 | Nagy | A61K 49/223 514/759 |
| 2014/0073027 A1 | 3/2014 | Dholakia et al. | |
| 2020/0297854 A1 * | 9/2020 | Ingber | A61P 7/02 |

FOREIGN PATENT DOCUMENTS

| | | |
|---|---|---|
| CN | 101381705 A | 3/2009 |
| EP | 3184624 A1 * | 6/2017 |
| WO | 2004-011616 A2 | 2/2004 |
| WO | 2018/026958 A1 | 2/2018 |

OTHER PUBLICATIONS

Xu et al. Formation of monodisperse microbubbles in a microfluidic device. AIChe journal. 2006, vol. 52, No. 6, pp. 2254-2259 (Year: 2006).*
Zhou et al ("Loading Trehalose Into Red Blood Cells by Electroporation and Its Application in Freeze-Drying," CryoLetters 31 (2), 147-156 (2010) (Year: 2010).*
"Flow-Through Microfluidic Device for High-Efficiency Transfection of Mammalian Cells Through Combined Microelectroporation and Sonoporation," A Thesis by Whitney Longsine, May 2011. available from Texas A&M Repository (Year: 2011).*
Carugo et al ("Contrast agent-free sonoporation: The use of an ultrasonic standing wave microfluidic system for the delivery of pharmaceutical agents," Biomicrofluidics 5, 044108 (2011) (Year: 2011).*
Wang et al. (Lab Chip. Aug. 21, 2010;10(16):2057-61. doi: 10.1039/c004472e. Epub Jun. 21, 2010.) (Year: 2010).*
Tlaxca et al. (Tlaxca, J. L. et al., "Analysis of in vitro Transfection by Sonoporation Using Cationic and Neutral Microbubbles," Ultrasound in Medicine and Biology, vol. 36, No. 11, 1907-1918 (2010).) (Year: 2010).*
Singh et al. (Res Pharm Sci. Jul.-Dec. 2010; 5(2): 65-77.) (Year: 2010).*
Longsine-Parker et al.; "Microfluidic electro-sonoporation: a multimodal cell poration methodology through simultaneous application of electric filed and ultrasonic wave"; Lab on a Chip, 2013, vol. 13, No. 11, pp. 2144-2152.
Fan et al.; "Mechanisms of microbubble-facilitated sonoporation for drug and gene delivery"; Therapeutic Delivery, 2014, vol. 5, No. 4, pp. 467-496.
Mulvana et al.; "Ultrasound assisted particle and cell manipulation on-chip"; Advanced Drug Delivery Reviews, 2013, vol. 65, Nos. 11-12, pp. 1600-1610.

(Continued)

Primary Examiner — Christopher M Babic
Assistant Examiner — Joel D Levin
(74) Attorney, Agent, or Firm — ALGM LLP; Harry J. Guttman

(57) ABSTRACT
Provided herein are systems and methods for molecule delivery into cells. The method may include steps of forming a solution comprising an amount of microbubbles, an amount of soluble molecules, and one or more cells, flowing the solution through a microfluidic device, and sonicating the solution for a period of time sufficient to form pores in the one or more cells. In particular, such methods may be used for preservation of cells through delivery of a preservation agent.

15 Claims, 8 Drawing Sheets

(56)          References Cited

OTHER PUBLICATIONS

Segers, et al.; "Acoustic bubble sorting for ultrasound contrast agent enrichment"; Lab on a Chip, 2014, vol. 14., No. 10, pp. 1705-1714.

Crowe et al: "Stabilization of Dry Mammalian Cells: Lessons from Nature", Integrative and Comparative Biology, vol. 45, No. 5, pp. 810-820, Nov. 2005.

Dixon et al: "Enhanced Intracellular Delivery of a Model Drug Using Microbubbles Produced by a Microfluidic Device", Ultrasound in Medicine and Biology, vol. 30, No. 7, pp. 1267-1276, Jul. 2013.

Longsine-Parker et al: "Microfluidic electro-sonoporation: a multimodal cell poration methodology through simultaneous application of electric filed and ultrasonic wave", Lab On a Chip, vol. 13, No. 11, pp. 2144-2152, Jan. 2013.

Wang et al: "Vortex-assisted DNA delivery", Lab On a Chip, vol. 10, No. 16, p. 2057, Jan. 2010.

Bhutto et al. (2018) "Effect of Molecular Weight on Sonoporation-Mediated Uptake in Human Cells" Ultrasound Med Biol., vol. 44, No. 12, pp. 2662-2672.

Murphy et al. (2020) "Delivery of thymoquinone to cancer cells with as1411-conjugated nanodroplets" PLoS One, vol. 15, No. 5, Article e0233466 (13 pages).

* cited by examiner

| Interdigital Transducer | Microfluidic channel | Interdigital Transducer |
|---|---|---|

320

310

330

342

340

344

Post-Sonoporation Cell Recovery
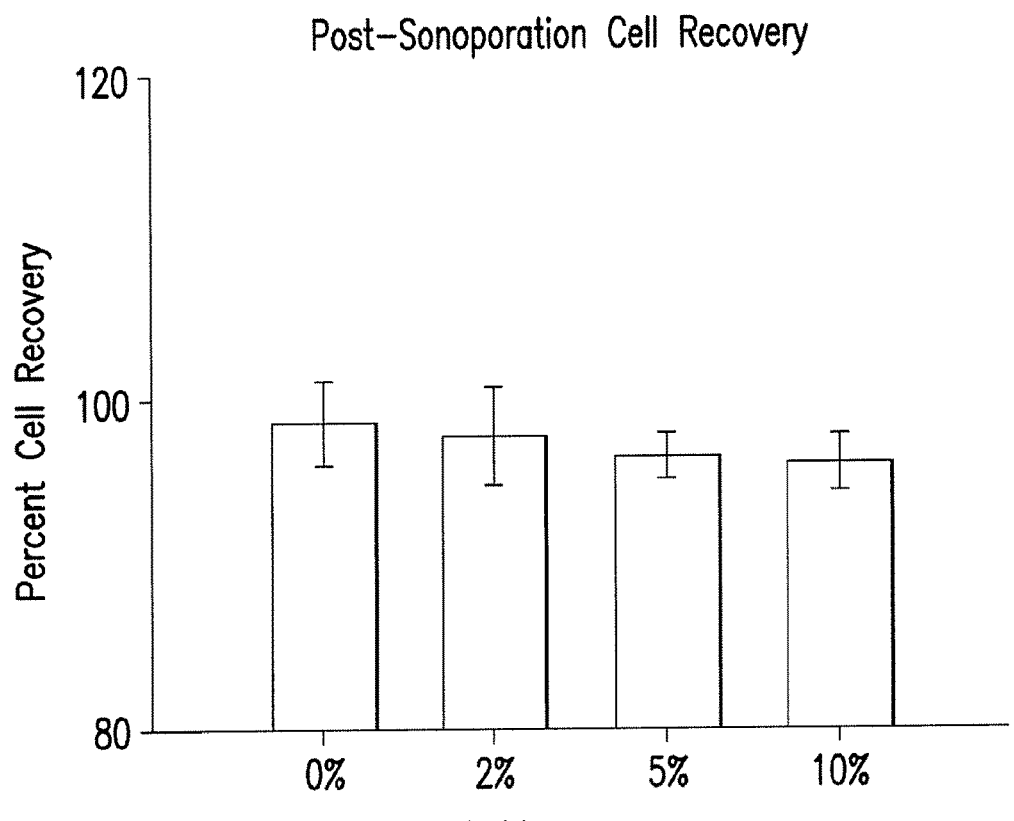
FIG.4
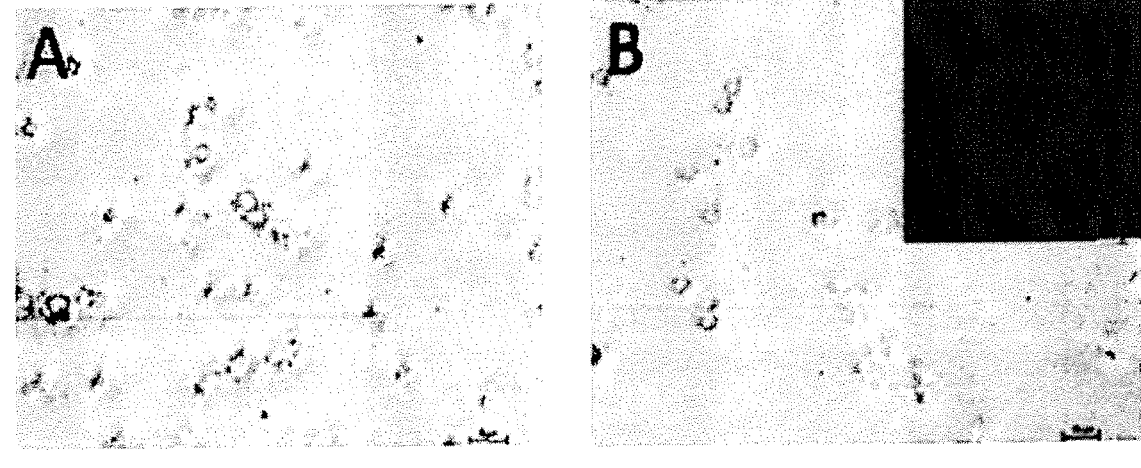
FIG.5A                    FIG.5B

SYSTEMS AND METHODS FOR PRESERVATION OF CELLS

STATEMENT OF GOVERNMENT SUPPORT

This invention was made with government support under U01 HL127518 awarded by the National Institutes of Health and IOS1659970 awarded by the National Science Foundation. The government has certain rights in the invention.

TECHNICAL FIELD

The presently-disclosed subject matter generally relates to systems and methods for the delivery of molecules into cells. In particular, certain embodiments of the presently-disclosed subject matter relate to systems and methods for the preservation, for example cryopreservation and lyopreservation, of cells that make use of ultrasound and sonoporation.

BACKGROUND

Red blood cells (RBCs) perform a vital role by delivering molecular oxygen to tissues throughout the body in order to meet the metabolic needs of the body. Conditions or procedures that cause significant loss of functional RBCs, such as trauma, blood disorders, cancer treatment, or surgical procedures, can lead to oxygen deprivation, life-threatening organ failure, and can eventually lead to death. Therefore, many patients require blood transfusions in order to replace lost RBCs and maintain adequate oxygenation of tissues. According to the Agency for Healthcare Research and Quality, blood transfusions are the most common medical procedure performed in U.S. hospitals, with over 2.9 million patients receiving a combined total of over 13.7 million units of RBCs in 2011. Approximately 85 million units of RBCs are transfused annually worldwide, and the global market size for blood preparation was $44 billion in 2015.

Despite the amount of RBCs utilized each year, limitations in RBC preservation pose a significant challenge to transfusion medicine. RBCs are typically stored at 4° C. and must be used within 42 days. Thus, frequent blood donations are needed in order to maintain an adequate supply of RBCs for transfusions. Over 370,000 units of expired RBCs were discarded in the United States in 2011 and over 10% of surveyed U.S. hospitals reported at least one day of blood shortage per year, with an average annual RBC shortage of 19 days in these hospitals. In some special cases, RBCs can be frozen in the presence of glycerol for up to 10 years, but the glycerol must be thoroughly removed via multiple cumbersome washing steps prior to transfusion, and most hospitals do not have the capability to perform this process. Furthermore, blood transfusions are also needed in places where refrigeration or freezing of RBCs is not available, such as in the field during military operations or at medical centers in remote locations. In many cases, ambulances are also not equipped to carry RBCs. Therefore, an effective method to store RBCs in a dried state for long-term preservation at ambient temperature would be highly beneficial and would provide increased access to blood products.

SUMMARY

One aspect of the disclosure provides a system for molecule delivery into cells, comprising a microfluidic device comprising a first channel for housing one or more microbubbles, a second channel for housing soluble molecules, the second channel in fluid communication with and intersected by the first channel, and a third channel for housing a cell solution, the third channel in fluid communication with and intersected by the second channel; and an ultrasound transducer positioned below the third channel or an interdigital transducer positioned on opposite sides of the third channel. In some embodiments, at least a portion of the third channel is in a spiral configuration. In some embodiments, the first channel, the second channel, and/or the third channel is about 20 μm to about 700 μm wide and about 20 μm to about 400 μm deep.

Another aspect of the disclosure provides a method for molecule delivery into cells, comprising forming a solution comprising an amount of microbubbles, an amount of soluble molecules, and one or more cells; flowing the solution through a microfluidic device 4; and sonicating the solution for a period of time sufficient to form pores in the one or more cells. In some embodiments, the soluble molecules are selected from the group consisting of trehalose, sucrose, sorbitol, xylitol, myo-iositol, diglycerol phosphate, proline, ectoine, taurine, hypotaurine, and transgenic expressed group 1, group 2, or group 3 Late Embryogenesis Abundant (LEA) proteins from the brine *Artemia franciscana*. In some embodiments, the method further comprises a step of drying and/or freezing the one or more cells. In some embodiments, the one or more cells are red blood cells.

Another aspect of the disclosure provides a method for the cryopreservation of cells, comprising forming a solution comprising an amount of microbubbles, an amount of preservation agent, and one or more cells; and sonicating the solution for a period of time sufficient to form pores in the one or more cells.

Another aspect of the disclosure provides a method for molecule delivery into cells, comprising passing a fluid comprising an amount of microbubbles, an amount of soluble molecules, and one or more cells through a microchannel one cell at a time and sonicating the cells as the cells pass through the microchannel such that the microbubbles form pores in the one or more cells through which one or more of the soluble molecules enter the one or more cells.

BRIEF DESCRIPTION OF THE DRAWINGS

FIG. 4 is a graph showing recovery of RBCs 24 hours after sonoporation, indicating minimal toxicity with this treatment.

FIG. 5A-B includes microscopic images of dried red blood cells without trehalose (A) and after loading with trehalose (B). Blood cells maintain shape after rehydration as shown in confocal image (B); no intact cells were found after rehydration without loading of the sugar (data not shown).

DETAILED DESCRIPTION

Figure 1:
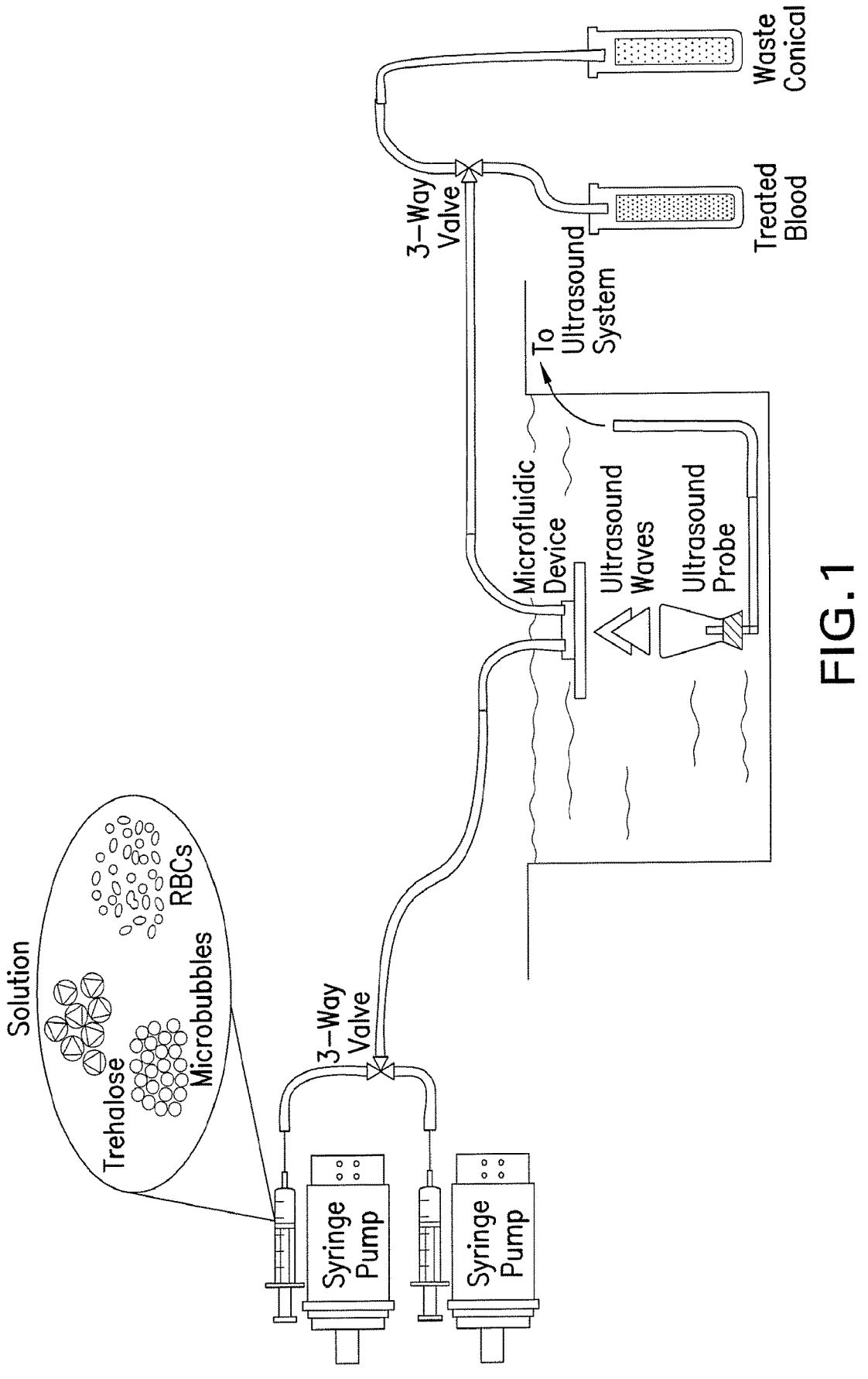
FIG. 1 is a schematic diagram showing an example molecule delivery system according to some embodiments of the disclosure.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

Embodiments of the disclosure provide a system and process for delivering molecules (i.e. a "target agent"), such as the cell protectant trehalose, into cells, such as RBCs or platelets, by utilizing a combination of ultrasound technology and microbubbles. Any type of cells, e.g. nucleated cells, are compatible with the systems and processes described herein. Exemplary cell types include, but are not limited to, stem cells which may be useful for stem cell therapy, insect cells e.g. for transgenic protein production, and cell lines for drug testing such as HepG2, CHO, HEK, HELA, etc.

Microbubbles, which are generally ~1-3 μm in diameter, are FDA approved for use as ultrasound contrast agents in clinical echocardiography, and are also in development for therapeutic use. Microbubbles oscillate in response to ultrasound pressure waves that cause the microbubbles to expand and compress with each positive and negative pressure cycle. This microbubble oscillation ("cavitation") exerts forces on the surrounding fluid. At sufficient ultrasound amplitudes the oscillation becomes non-linear and can induce strong microstreaming or microjetting effects in the surrounding fluid. When this occurs near a cell membrane the microjets and shock waves produced by microbubble cavitation can form transient pores in the membrane, which are generally rapidly repaired by the cell in less than a minute. Embodiments of the disclosure utilize this pore formation process ("sonoporation") to directly deliver target agents into the cell. In some embodiments, sonoporation may be used to deliver the sugar trehalose, a cell protectant, into RBCs to promote cell survival during freezing and drying.

In some embodiments, microbubbles comprise about 1-20% of a solution containing the target agent and/or cells.

In some embodiments, the microbubbles are lipid-coated. Exemplary lipids that may be utilized include, but are not limited to 1,2-distearoyl-sn-glycero-3-phosphocholine (DSPC), 1,2-dipalmitoyl-sn-glycero-3-phosphocholine (DPPC), 1,2-distearoyl-sn-glycero-3-ethylphosphocholine (DSEPC), 1,2-distearoyl-sn-glycero-3-phosphoglycerol (DSPG), 1,2-distearoyl-sn-glycero-3-phosphoetha-nolamine-N-[methoxy(polyethylene glycol)-2000] (DSPE-PEG2000), and/or polyethylene glycol-40 stearate (PEG-40). In some embodiments, a formulation comprising DSPC:DSEPC:DSPG:PEG-40 in a 100:43:1:4.5 molar ratio is used. In some embodiments, a lipid solution composed of 94:4 molar ratio (DPPC:DSPE-PEG2000) is used.

Trehalose has been granted Generally Recognized As Safe (GRAS) status by the U.S. Food and Drug Administration and is used for food preservation in products such as sweets, meats, and frozen foods. It is a naturally-occurring non-reducing sugar found in many plants and lower animals that helps them survive water-limited states such as dehydration or freezing. During freezing, trehalose prevents damage from ice crystals. During drying, the sugar forms a glassy barrier around cellular membranes replacing water. However, cells such as RBCs are generally impermeable to trehalose and must be manipulated to enable intracellular delivery of this compound. To date, various strategies have been tested to load trehalose into RBCs, including osmotic stress, rapid temperature changes, or electroporation, but these approaches have not been successful in producing functional RBCs that survive long-term preservation without significant loss of hemoglobin. However, it has now been surprisingly discovered that ultrasound and microbubbles can be utilized to induce transient pores in cellular membranes to facilitate active transport of molecules such as trehalose into cells. Further, it has been determined that sonoporation can be utilized in a microfluidic device system in order to effectively and consistently deliver sufficient amounts of trehalose into RBCs for long-term preservation in a dried state, which can then be re-suspended in sterile water, or another solution, prior to use for transfusion. The microfluidic system enables precise and consistent control over molecule delivery in order to increase the loading efficiency and viability of processed cells.

In some embodiments of the presently-disclosed subject matter, a system for delivery of a target agent into cells, e.g. for cell preservation, is thus provided that includes a microfluidic device and an ultrasound transducer (FIG. 1). For example, embodiments of the system are useful for cryopreservation and/or lyopreservation. Cryopreservation preserves cells by cooling to very low temperatures (e.g., lower than −80° C.) whereas lyopreservation is a biomimetic strategy based on anhydrobiosis to preserve cells at ambient temperatures in a desiccated state. This device can be used for sonoporation and loading of any soluble molecule, e.g. drugs, genes, proteins, or cellular labels (e.g. fluorescein) into any cells. With reference to FIG. 1, in some embodiments, the microfluidic device is positioned at or near the surface of a filled water tank. Tubing, such as Tygon PVC clear tubing (1/16 inch inner diameter, 1/8 inch outer diameter) (McMaster-Carr), may be inserted into the inlet and outlet ports of the device. The inlet tubing may lead to a 3-way valve with one side of the valve leading to a syringe filled with the sample solution (cells, trehalose, and microbubbles) clipped into a syringe pump (e.g. a NE-300 syringe pump, Farmingdale, NY, USA) and the other side leading to a wash phosphate buffered saline (PBS) solution, also clipped into a syringe pump. The outlet tubing may lead to another 3-way valve which splits to a waste and collection container.

Figures 2A, 2B:
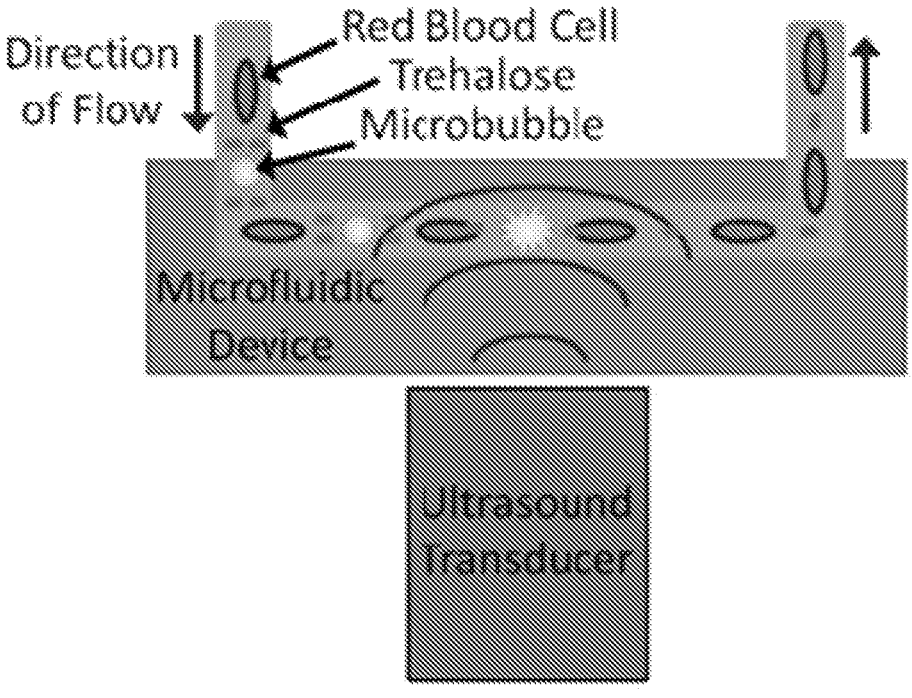
FIG. 2A-B is a schematic diagram showing an example ultrasound-integrated microfluidic device according to some embodiments of the disclosure.

As the solution comprising microbubbles, trehalose, and cells flows through the microfluidic device, the ultrasound transducer emits ultrasonic frequencies which induces microbubble oscillation and causes pore formation in the cell membrane which allows for the transport of trehalose through the transient pores into cells (FIG. 2A).

The microbubbles may be synthesized and then added to the samples prior to entering the microfluidic device. Alternatively, the microbubbles may be synthesized directly within the microfluidic device. For example, in some embodiments, microbubbles are generated inside the device using the compound octafluoropentane (OFP), which is FDA approved for clinical use in ultrasound contrast agents. In some embodiments, OFP and trehalose solutions are stored inside the device itself.

In some embodiments, liquid perfluorocarbon droplets are utilized to form microbubbles. Perfluorocarbon droplets are used in a liquid phase instead of a gas phase, typically with perfluoropentane (C5F12), which has a low boiling point (29° C. in bulk). The liquid droplets are typically 0.1-5 μm in diameter and can be vaporized into microbubbles in situ using ultrasound pulses as short as 1-5 μs. The microbubbles produced by vaporized droplets can be insonified to induce sonoporation similar to the microbubbles previously described.

In some embodiments, the solution comprising at least one of cells, microbubbles and the target agent/molecule comprises a PBS buffer. In some embodiments, a lactobi-onate-containing buffer is used. An exemplary lactobionate-containing buffer is shown in Table 1.

TABLE 1

| MiR05-Kit [1 vial] | Formula weight [g/mol] | Amount for 250 mL final volume [g] | Final concentration [mM] |
|---|---|---|---|
| EGTA | 380.4 | 0.05 | 0.5 |
| MgCl₂6H₂O | 203.3 | 0.155 | 3 |
| Lactobionic acid | 358.3 free acid | 5.375 | 60 |
| Taurine | 125.1 | 0.625 | 20 |
| KH₂PO₄ | 136.1 | 0.34 | 10 |
| HEPES | 238.3 | 1.19 | 20 |
| D-Sucrose | 342.3 | 9.41 | 110 |

In some embodiments, less than all of the listed components may be present and/or additional components may be added. Example concentration ranges that are compatible with the buffer described herein are shown in Table 2.

TABLE 2

| Component | Final concentration [mM] |
|---|---|
| EGTA | 0.1-0.9 |
| MgCl₂6H₂O | 0.6-5.4 |
| Lactobionic acid | 12-108 |
| Taurine | 4-36 |
| KH₂PO₄ | 2-18 |
| HEPES | 4-36 |
| D-Sucrose | 0-400 |
| Trehalose | 0-400 |

Figure 3:
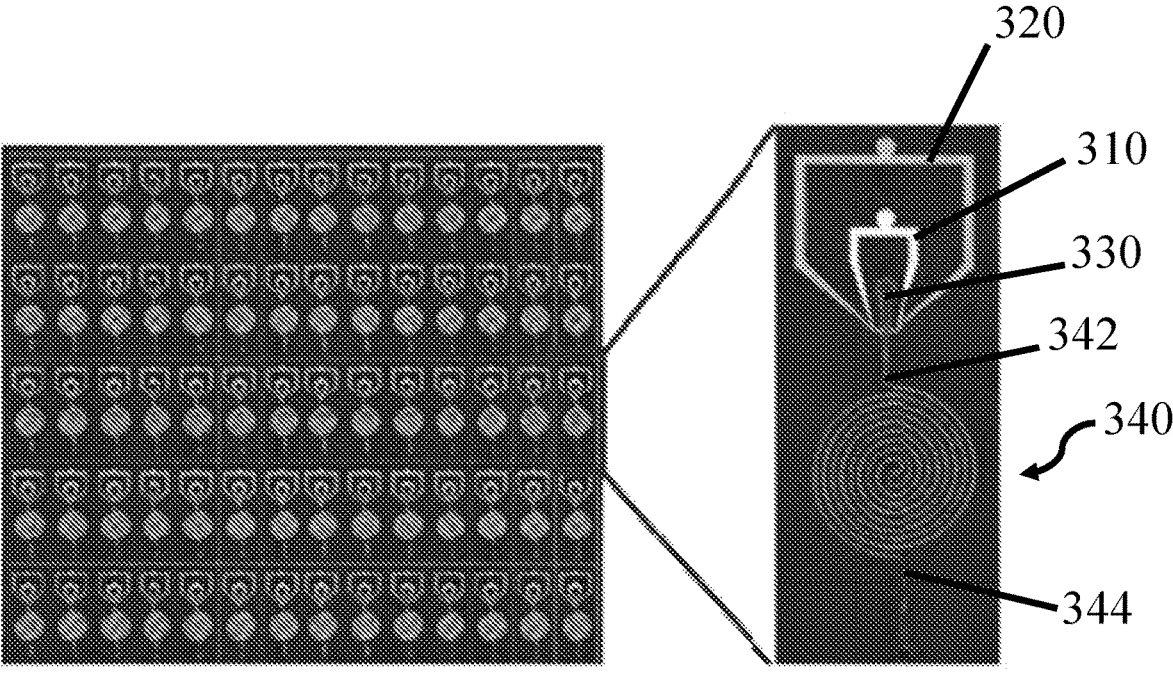
FIG. 3 is a schematic diagram showing an example microfluidic design according to some embodiments of the disclosure.

In some embodiments, a system comprising a collection of microfluidic devices with integrated ultrasound transducers is provided (FIG. 3). Cells flow through the devices where the cells are mixed with microbubbles and a target agent solution prior to sonication with ultrasound pulses to deliver the target agent into cells.

With reference to FIG. 3, in some embodiments, the microfluidic device is comprised of a first channel 310 for housing one or more microbubbles, a second channel 320 for housing a target agent, e.g. a preservation agent, and a third channel 330 for housing a cell solution. In some embodiments, the channels of the microfluidic device are arranged such that the second channel 320 is in fluid communication with and intersected by the first channel 310, and the third channel 330 is intersected by and in fluid communication with the second channel 320 (and the first channel 310). In some embodiments, an ultrasound transducer is positioned below the third channel, and, in some embodiments, at least a portion of the third channel is in a spiral configuration 340. Other designs are suitable for the third channel 330, such as a snake-like shape. In some embodiments, interdigitated transducers (IDTs) are placed on each side of the third channel to generate surface acoustic waves in the device by generating periodically distributed mechanical forces via a piezoelectric effect (FIG. 2B). In some embodiments, the first channel 310, the second channel 320, and/or the third channel 330 is about 20 μm to about 700 μm wide and about 20 μm to about 400 μm deep. In some embodiments, the first channel 310, the second channel 320, and/or the third channel 330 is about 200 μm to about 500 μm wide.

The submillimeter channels of the microfluidic device allow for a homogeneous mix of cells, the soluble molecule to be delivered to the cells, and microbubbles to flow through while being treated with ultrasound. The thin layer of cells required by the channel size also helps avoid attenuation problems caused by high concentrations of microbubbles and cells while being treated with ultrasound. This also increases consistency of molecule uptake, as all the cells in line with the ultrasound transducer can be treated simultaneously and not be blocked by others.

Various flow rates can be used in the microfluidic device, such as about 5-40 ml/hr. Various known methods may be used to fabricate the microfluidic device. In some embodiments, the device is fabricated using a photoresist as described in Example 2. An alternate method involves using deep reactive ion etching ("DRIE.") with the Bosch process to etch channels directly into silicon instead of using photoresist. Glass can be bonded onto the silicon using anodic bonding and holes are drilled into the devices for inlet/outlet ports. This approach requires more effort/cost per device but each device may be more durable.

In some embodiments, ultrasound pulses may be generated by piezoelectric crystals, which convert electrical energy into acoustic pressure waves. These materials are used in audio speakers and also in ultrasound transducers for medical imaging (e.g. a Philips P4-1 ultrasound probe on a Verasonics Vantage 64LE ultrasound system). The thickness of the crystal determines the fundamental frequency, which is below 20 kHz for audio equipment and generally above 1 MHz for clinical ultrasound imaging applications. The optimal ultrasound frequency for sonoporation depends on the microbubble properties but is typically in the range of 1-5 MHz. In some embodiments, a frequency of about 2.5 MHz is used. In some embodiments, frequencies up to 50 MHz may be used to induce sonoporation within the microfluidic device. Higher frequencies (>10 MHz) are generally not used in medical imaging due to the fact that ultrasound absorption by tissue increases with frequency, so it is difficult to image deeper tissues at high frequencies. In the microfluidic device, however, penetration depth is not a significant issue. Microbubbles have a resonance frequency based on their size and shell properties, and in some embodiments, the ultrasound frequency for sonoporation is generally the same as the microbubble resonance frequency. In most cases, microbubble resonance frequencies are in the range of 1-3 MHz. The ultrasound pressure amplitude is another variable in sonoporation. Generally, pressures between 0.1-5 MPa are used, e.g. between 0.5-2 MPa. The ultrasound pulse duration is an additional parameter relevant to sonoporation. Pulse durations of 1-1000 μm is can be used without generating significant heating. In some embodiments, a pulse duration of about 2 μs is used. In some embodiments, piezoelectric crystals may be integrated within the microfluidic device in order to generate the ultrasound waves for sonoporation. In some embodiments, the total time of sonication (including ultrasound pulses) is at least about 1-100 seconds, for example, at least about 8-10 seconds. In some embodiments, continuous ultrasound is employed to generate standing acoustic waves. Acoustic radiation force causes cells to move toward specific nodes in standing acoustic waves within each channel which enables consistent sonoporation of each cell as it passes through the device.

In some embodiments, the microfluidic devices of the presently-disclosed subject matter, can be utilized as a stand-alone automated system that is used by hospitals and blood banks to process RBCs for long-term preservation in a frozen or dry-preserved state. In most cases, blood is collected into special collection bags and centrifuged to separate components (i.e. plasma, platelets, RBCs) from each other. After component separation and optional leukocyte reduction to reduce white blood cell levels, packed RBCs are stored at 4° C. for up to 42 days, or in rare cases RBCs are frozen in the presence of glycerol. In making use of the devices of the presently-disclosed subject matter, however, users are able to attach a bag of packed RBCs that will be pumped through the system and processed inside the chamber before exiting into a separate collection bag that can be frozen or dry-processed using convective drying, spray-drying, or standard freezing/freeze-drying protocols.

Further provided, in some embodiments of the presently-disclosed subject matter are methods for cryopreservation of cells. In some implementations, a method for the cryopreservation of cells is provided that comprises the steps of forming a solution including an amount of microbubbles, an amount of a preservation agent, and one or more cells; and sonicating the solution for a period of time sufficient to form pores in the one or more cells. In some implementations, the preservation agent is selected from: carbohydrates, such as trehalose and sucrose; polyols, such as sorbitol, xylitol; cylitols, such as myo-iositol; anionic polyols, such as diglycerol phosphate; amino acids and derivatives, such as proline, ectoine, taurine, and hypotaurine; and anhydrobiosis related proteins, such as transgenic expressed Late Embryogenesis Abundant (LEA) proteins from the brine *Artemia franciscana* (groups 1, 3, and 6). In some embodiments, the preservation agent is selected from the group consisting of trehalose, sucrose, sorbitol, xylitol, myo-iositol, diglycerol phosphate, proline, ectoine, taurine, hypotaurine, and transgenic expressed Late Embryogenesis Abundant (LEA) proteins from the brine *Artemia franciscana* (groups 1, 3, and 6).

In some embodiments, to facilitate long-term storage and preservation of the one or more cells, the cryopreservation method further comprises the step of drying the one or more cells, such as by freeze drying. In some embodiments, the cells are frozen without drying. In some embodiments, the one or more cells are red blood cells.

The presently-disclosed subject matter is further illustrated by the following specific but non-limiting examples. Some of the following examples are prophetic, notwithstanding the numerical values, results and/or data referred to and contained in the examples. The following examples may also include compilations of data that are representative of data gathered at various times during the course of development and experimentation related to the present invention.

Example 1. Microbubbles

As shown in Table 3, microbubble products are commercially available.

TABLE 3

| | | | Shell | |
| Product Name | Vendor | Approval Status | Composition | Gas Composition |
|---|---|---|---|---|
| DEFINITY ® | Lantheus Medical Imaging | Approved in US, Europe, and parts of Asia | Lipid | Octafluoropropane |
| SONOVUE ® | Bracco | Approved in North America, Europe | Lipid | Sulfur hexafluoride |
| SONAZOID ® | GE | Approved in Japan and Korea | Lipid | Perfluorobutane |
| OPTISON ® | GE | Approved in US and Europe | Denatured albumin | Octafluoropropane |

Commercially available microbubble products.

For these studies, lipid-coated microbubbles were synthesized using a straightforward process. The lipid shell is prepared in order to stabilize the microbubble and an inert gas with low solubility in water (such as perfluorocarbon) is used to also promote microbubble stability. To synthesize microbubbles a lipid solution was first prepared. Many different possible formulations would be feasible for this application, but in this example, a formulation comprising DSPC:DSEPC:DSPG:PEG-40 in a 100:43:1:4.5 molar ratio was primarily used. The lipids are mixed in an organic solvent (i.e. chloroform) which is then evaporated to form a dry lipid film. The lipid film is rehydrated with water or a buffer such as phosphate-buffered saline (PBS) and sonicated with a probe sonicator to disperse the lipids. The exact sonication parameters can be varied as long as the lipid solution is completely dispersed, as indicated by the appearance of a clear solution. Next, the lipid solution is placed in a 1.5 ml glass vial, capped and sealed with a septum cap and crimping tool. The head space of the vial is filled with the gas via 2 needles (1 for input and 1 for venting air) that are inserted through the septum. After filling the head space, the vial is amalgamated using a standard amalgamator for 15-45 seconds. This shakes the solution and entrains gas bubbles into the liquid where the lipids spontaneously coat the surface and stabilize the microbubbles. Perfluorobutane gas (C4F10) was used, but any inert gas with low solubility in water is adequate. After amalgamation, the microbubbles are ready for use. They can be stored at 4° C. for up to a day. The microbubbles may be synthesized as described and then added to the samples prior to entering the microfluidic device. In other embodiments, the microbubbles may be synthesized directly within the microfluidic device.

Example 2. Microfluidic Sonoporation Device

A microfluidic sonoporation device is developed to improve consistency and precision of trehalose loading in red blood cells. This device can be used for sonoporation and loading of any soluble molecules into any cells. In previous studies, a solution containing trehalose (200-400 mM), microbubbles, and red blood cells was added into a 15 ml conical tube (total sample volume of 0.5 ml), placed in a water tank, and ultrasound pulses were applied for 70 seconds to induce sonoporation and trehalose delivery. However, in this setup the microbubbles and cells are distributed throughout the sample and do not consistently interact. The microfluidic sonoporation device enables more consistent interaction of microbubbles and cells at precise locations. An example of the device design is shown in FIG. 3. In this design, a channel 310 containing perfluorocarbon gas intersects with a channel 320 containing trehalose solution. The gas passes through a 10-μm orifice before entering the trehalose solution, where the gas will break apart into small bubbles at a consistent rate. Note that no surfactant (lipid) is needed in this design, because the microbubbles will be insonified by ultrasound within seconds before they dissolve. The microbubble/trehalose solution intersects with the channel 330 containing the cell solution, which enters a spiral patterned channel 340. The centrifugal force generated as the solution passes through the spiral pattern will push the cells and microbubbles toward the outer wall so that they are in near proximity when ultrasound is applied, thereby enhancing sonoporation efficiency. FIG. 3 shows inward-flowing channels 342 and outward-flowing channels 344. Other designs are possible, such as a snake-like shape. The ultrasound transducer, or piezoelectric crystal, is placed directly below the spiral pattern. In this example, each channel is 100 μm wide and 50 μm deep, although these dimensions can be adjusted down to a minimum size of 20-30 μm (cells may become trapped if the dimensions are smaller than 20 μm).

There are multiple options for fabrication of the devices. In the present example, fabrication begins by creating a photomask of the device design. Photoresist (SU8-2050) is coated on a silicon wafer at a thickness of 50 μm, the photomask is aligned over the wafer with a mask aligner, and the wafer is exposed to ultraviolet light to crosslink the photoresist in the exposed sections. After processing with a developer solution, the wafer is ready for use as a mold. Polydimethylsiloxane (PDMS) is poured over the wafer mold and baked at 60° C. for 2 hours to cure. The PDMS is removed off the wafer mold and each device is cut away from the rest of the cured PDMS. Holes are punched with a 2.5 mm hole-puncher to create the inlet/outlet ports. The devices are placed in a plasma asher for 1 minute and immediately bonded onto glass slides. Plastic tubing is placed in the holes and connected to syringes, which are automatically depressed in a syringe pump at the desired flow rate.

Example 3. Cryopreservation of Red Blood Cells

Figure 6A:
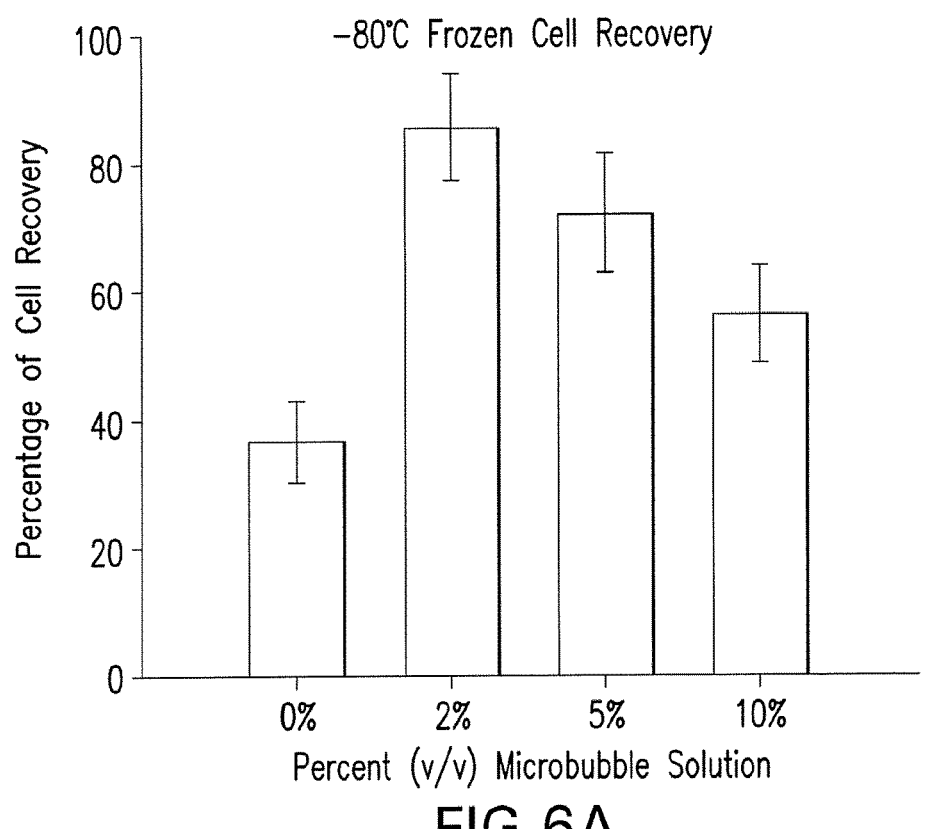
FIG. 6A-B includes graphs showing recovery of RBCs following freezing/thawing (A) or freeze-drying/rehydration (B), indicating significantly increased recovery in samples with sonoporation treatment.
Figure 6B:
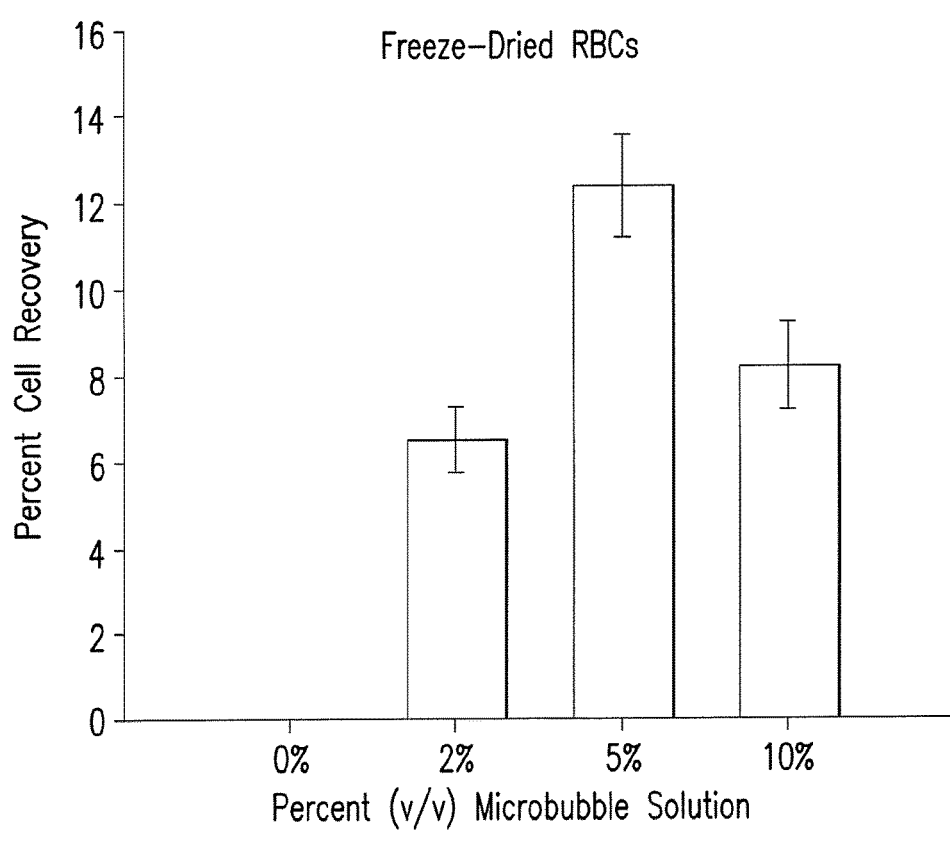

In vitro experiments have been performed to validate the methods and systems described herein. Briefly, a 0.5 mL solution containing pig or human RBCs, 200 mM trehalose, and microbubbles was placed in a conical tube and sonicated with a 2.5-MHz clinical ultrasound probe for 70 seconds (Philips 4-1 on a Verasonics Vantage 64LE ultrasound imaging system). High cell recovery (>95%) was obtained 24 hours after sonication (FIG. 4), indicating that this treatment causes minimal toxicity. Following sonication, samples were dried (FIG. 5A-B), frozen at −80° C., or freeze-dried for 1 week. Upon thawing or rehydration, the percentage of structurally intact RBCs was counted (FIG. 6A-B). Cell recovery rates of up to 85% were achieved after freezing/thawing, compared to less than 40% without sonoporation. Cell recovery rates of up to 12% were achieved after freeze-drying/rehydration, compared to 0% without sonoporation. Although the recovery is still low, this was believed to be a significant result given that not a single RBC was recovered from freeze-dried samples that had not been treated with sonoporation. In addition, improved freeze-drying techniques can increase recovery, as initial experiments resulted in recovery of less than 8% (data not shown), but even with small changes to the cell media composition and freeze-drying parameters the recovery rate increased above 12%, while the recovery rate for frozen cells was above 85%. The microfluidic sonoporation device can further improve the recovery rates by enabling consistent and precise trehalose delivery to each cell. This device is also effective in processing RBCs for long-term preservation in a frozen or freeze-dried state.

Example 4. Molecule Delivery into Cells

Methods

Source and storage conditions of human RBCs. The Red Blood Cells were acquired from Innovation Research (Omaha, NE, USA) and stored in CPD-AS1 solution at 4° C. for up to 42 days.

Microbubble synthesis methods. Microbubbles were synthesized for ultrasound usage. The microbubbles were composed of a gas perfluorocarbon core surrounded by a lipid shell. Phospholipids were obtained from Avanti Polar Lipids (Alabaster, AL, USA). The microbubble lipid solution was composed of DSPC:DSEPC:DSPG:PEG-40 in a 100:43:1:4.5 molar ratio. Lipids were dissolved in chloroform and the solvent was evaporated under argon. The dry lipid film was rehydrated in PBS to a concentration of 5 mg/mL.

To produce microbubbles, the prepared lipid solution was diluted 4× in PBS in a clear 11 mm glass crimp vial and sealed with a 10 mm target septa and 11 mm tapones crimp, all from VWR (Radnor, PA, USA). The remaining air in the vial was replaced with decafluorobutane (Fluoromed, Round Rock, TX, USA) via a hypodermic needle (Becton Dickinson, Franklin Lakes, NJ, USA) and a second needle to vent. The vial was then mixed by a high-speed amalgamator for 30 s at 4350 CPM (Pelican)

Microfluidic device design/fabrication. Fabrication of mask/wafer:

Premade 3 inch diameter silicon wafer

Photoresist materials (SU8-3035, SU8-2050)

Propylene glycol monomethyl ether acetate—mask development

Isopropanol—wash the wafer

To create the PDMS device, a 10:1 mixture of base to curing agent was combined and mixed well (SYLGARD® 184 Silicone Elastomer Kit, Down Corning Corporation, Midland, MI). The mixture was desiccated for 1 hour to remove air bubbles and poured over the silicon wafer in a petri dish. The covered wafer was then baked for 2 hours at 60° C. Once cured, the device was cut to size using a straight razor and inlet/outlet holes were created using a 2.5 mm sampling tool (WellTech Rapid-Core). The PDMS piece was then plasma bonded to a glass side (100V for 60 s, 500 mbar $O_2$) using an Axic HF-8 plasma asher. To set up for testing, the device was held with clamps and ring stands at the surface of a filled 20-gallon water tank (FIG. 1). A segment of Tygon PVC clear tubing (1/16 inch inner diameter, 1/8 inch outer diameter) (McMaster-Carr) was inserted into the inlet and outlet ports of the device. The inlet tubing lead to 3-way valve. One side of the valve lead to a syringe filled with the testing solution, clipped into a NE-300 syringe pump (Farmingdale, NY, USA). The other side led to a wash PBS solution, also clipped into a syringe pump. The outlet tubing lead to another 3-way valve which split to a waste and collection conical vial.

Ultrasound setup and methods. A P4-1 ultrasound transducer (Ultra Solutions, USA) was clamped in place in the water, below the device, with the acoustic lens facing the surface of the water. The ultrasound was used in Flash Mode with pressures ranging from 0-1.8 MPa peak negative pressure. The focus is 40 mm from the acoustic lens.

Fluorescein Assay. The stock blood solution was diluted 40× in fluorescein (VWR) solution and PBS. The mixture was next pipetted into 1 mL aliquots and aspirated into a syringe (VWR) with the use of a hypodermic needle. The appropriate amounts of microbubbles were added shortly before running the samples on the device. The 1 mL aliquot was flowed through the device at the appropriate ultrasound settings and flow rate (10-40 mL/h) and collected into a conical vial at the end. The collection was washed 3× with 1 mL of PBS and a final volume of 200 μL of PBS was added after washing. The samples were kept on ice or in a 4° C. refrigerator until flow cytometry analysis could take place.

Trehalose Assay. The stock blood solution was diluted 40× in PBS with dissolved trehalose at a concentration of 171 mg/mL. It was pipetted into 1 mL aliquots and aspirated into a syringe with the use of a hypodermic needle. The appropriate amount of microbubbles were added shortly before running the sample on the device. The 1 mL aliquot was flowed through the device at the appropriate ultrasound settings and flow rate and collected into a conical vial at the end. The collection was washed 3× with 1 mL of PBS and a final volume of 100 μL of 0.1% Triton X-100 was added after washing. The samples were incubated for a minimum of 30 minutes, vortexed, and a trehalose assay kit was used to analyze results. (Megazyme, Bray, Co., Wicklow, Ireland)

Freeze/Thaw Experiment. The stock blood solution was diluted 40× in PBS with dissolved trehalose at a concentration of 171 mg/mL. It was pipetted into 1 mL aliquots and aspirated into a syringe with the use of a hypodermic needle. The appropriate amount of microbubbles were added shortly before running the sample on the device. The 1 mL aliquot was flowed through the device at the appropriate ultrasound settings and flow rate and collected into a conical vial at the end. The collection was not washed, but rather mixed by pipetting and 0.5 mL of the sample was placed in a cryovial and frozen down to −80° C. with the help of a COOL-CELL® box by Biocision. (San Rafael, CA, USA) After a minimum of 24 hours at −80° C., samples were removed from the freezer and thawed. About 40% of the sample was used for a calcein-AM/flow cytometry assay and the remaining 60% for a hemoglobin assay.

Flow cytometry methods. Flow cytometry was run on a MACSQUANT® Analyzer 10 (a flow cytometer by Miltenyi Biotec) for 10,000 events. Data was analyzed using FLOWJO® software. The gate was created by forward and side scattering of a control sample on the log scale and copied to the remaining samples. The mean FITC fluorescence was calculated from the gated cells and also copied to the remaining samples. This data was then transferred to MICROSOFT® Excel, averaged and graphed.

Trehalose assay. Completed as described in Trehalose Assay Kit by Megazyme (Bray, Co., Wicklow, Ireland).

BCA assay. Completed as described in BCA Protein Assay Kit II by BioVision Inc. (Milpitas, CA, USA).

Calcein-AM assay. Calcein-AM (1 mg/mL in DMSO) was diluted 1:10 in 1×PBS. The diluted solution was added to 200 µL of processed red blood cells. The final calcein-AM concentration was 5 µM. The samples were incubated for 30 minutes in a 37° C. water bath and placed on ice until ready for flow cytometry. Flow cytometry was run on a MACSQUANT® Analyzer 10 (a flow cytometer by Miltenyi Biotec) for 10,000 events. Data was analyzed using FLOWJO® software. Control samples (RBCs diluted 20× with no calcein-AM) were run to analyze the samples against. The control cells were gated based on forward and side scattering. The calcein fluorescence histogram was then gated so that any cell with a higher fluorescence level indicated viability. These percentages were then graphed.

Hemoglobin assay. In a 96-well plate, blank and calibration wells were created by adding water in one well and a 4:1 ratio of water:calibrator in another well. The samples were mixed in a 4:1 ratio of reagent:blood sample in separate wells. The samples were read at 400 nm wavelength on a plate reader at least 5 minutes after mixing.

Statistical analysis. Statistical comparisons between experimental and control groups were determined using a Student's t-test, with statistical significance defined as $p < 0.05$ (two-tailed). Bars represent mean±standard deviations.

Results

Figures 7A, 7B:
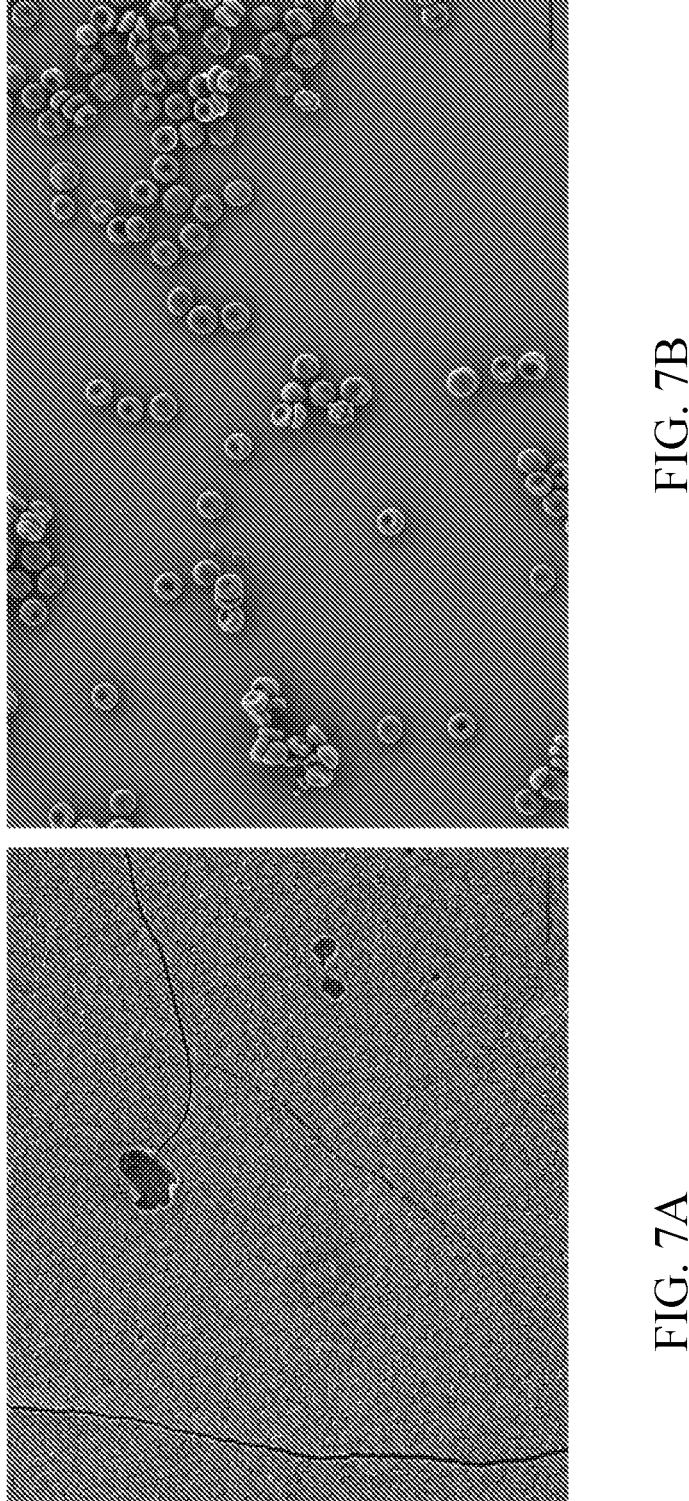
FIG. 7A-B includes scanning electron microscopy images of RBCs that were rehydrated after 6 weeks of dry storage at ambient temperature. (A) Rehydrated RBC samples without ultrasound treatment and (B) rehydrated RBCs after trehalose loading with ultrasound. Scale bars represent 10 μm.

FIG. 7A-B shows SEM images of RBCs that were rehydrated after 6 weeks of dry storage at ambient temperature.

Figure 8:
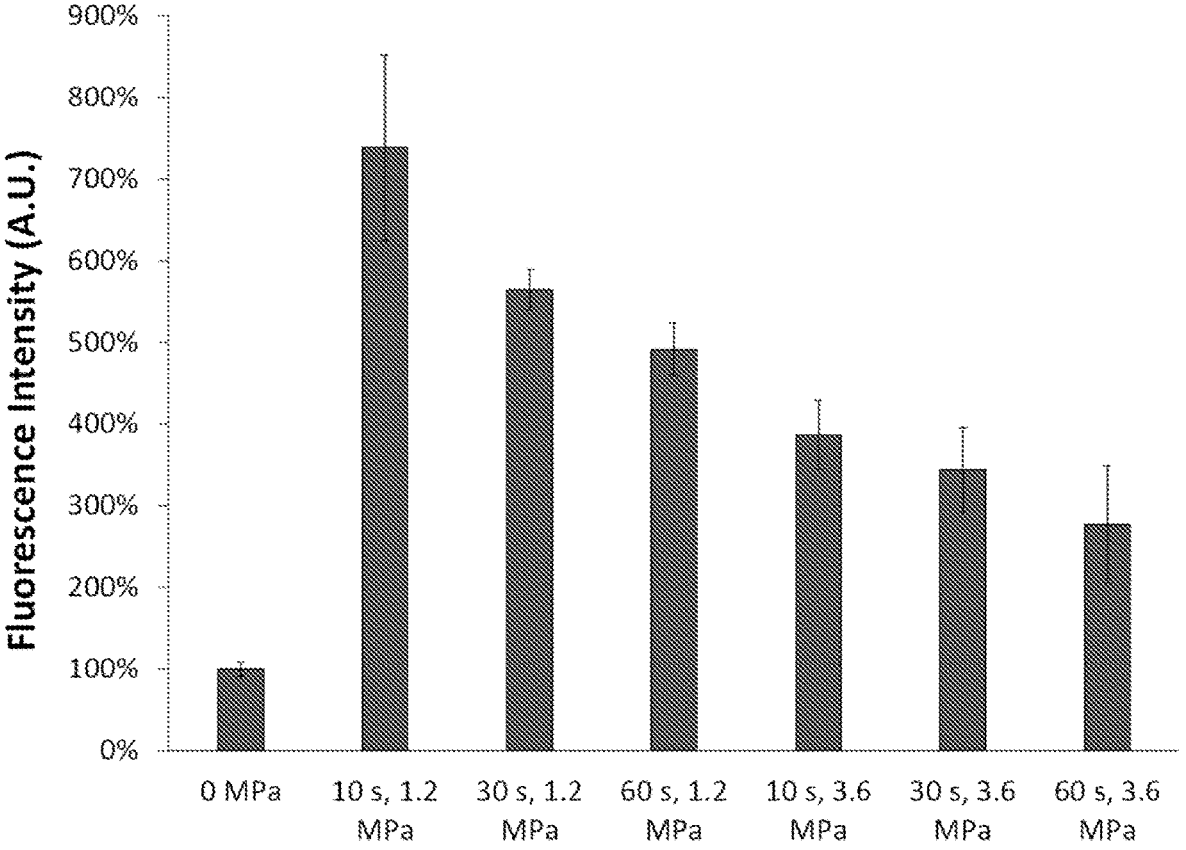
FIG. 8 is a graph showing the effect of sonication time and pressure on fluorescein delivery into RBCs.

It was found that increasing sonication times decreased the efficiency of fluorescein delivery while a pressure of 1.2 MPa had greater efficiency of fluorescein delivery than a pressure of 3.6 MPa (FIG. 8).

Figure 9A:
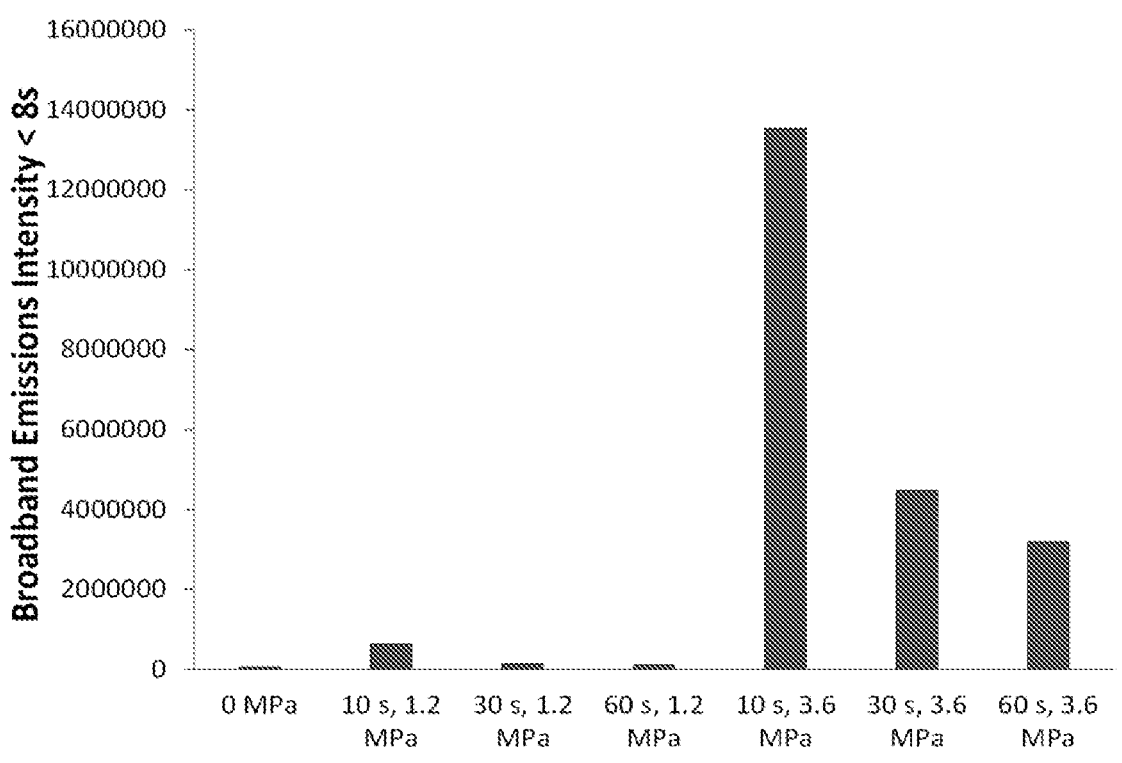
FIG. 9A-B includes graphs showing the broadband emissions intensity during the first 8 seconds of sonication (A) and after 8 seconds of sonication (B).
Figure 9B:
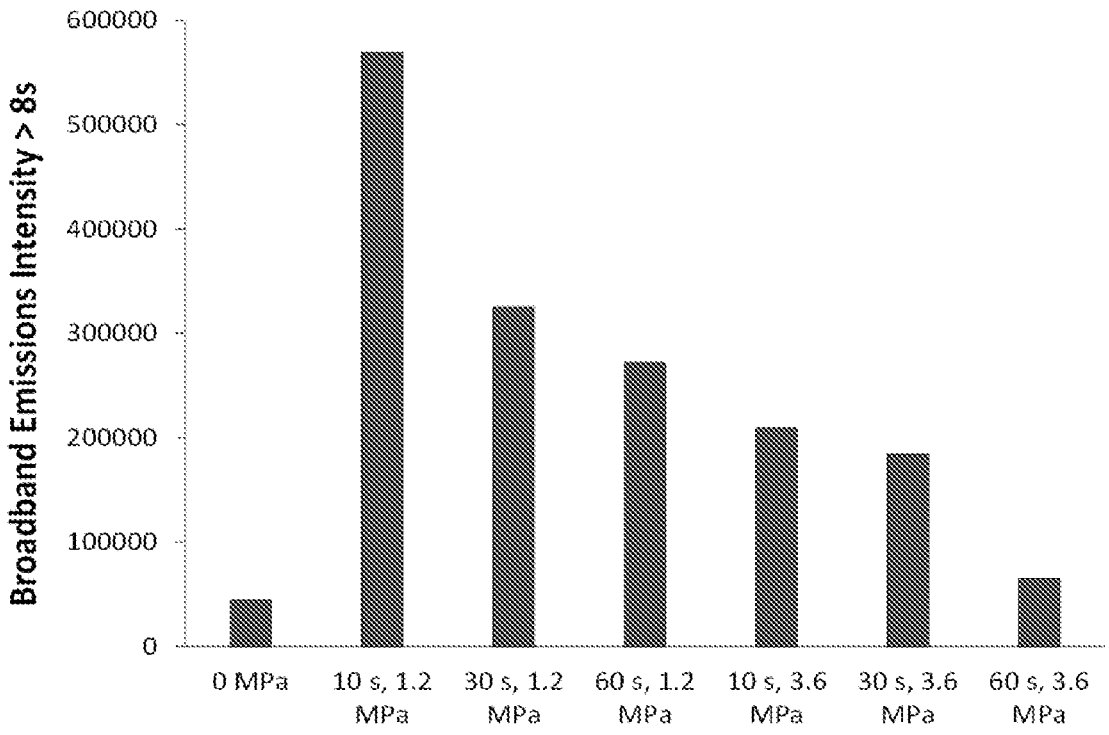

Microbubbles were added to erythrocyte solutions and sonicated (2.5 MHz, 4 cycles) at various pressures and durations. Fluorescence was quantified with flow cytometry. The amplitude of broadband emissions in the first 8 seconds of sonication did not correlate with delivery ($r^2 = 0.23$), whereas after 8 seconds the broadband emissions amplitude was associated with increased delivery to erythrocytes ($r^2 = 0.97$) (FIG. 9A-B). These results suggest that the timing of cavitation activity, rather than the amplitude alone, may be an important factor in ultrasound-mediated delivery of compounds into erythrocytes.

All publications, patents, and patent applications mentioned in this specification are herein incorporated by reference to the same extent as if each individual publication, patent, or patent application was specifically and individually indicated to be incorporated by reference, including the references set forth in the following list.

REFERENCES

1. Pfuntner, A., et al., Most Frequent Procedures Performed in U.S. Hospitals, 2011. HCUP Statistical Brief #165. October 2013. Agency for Healthcare Research and Quality, Rockville, MD. hcupus. ahrq.gov/reports/statbriefs/sb165. pdf 2. Whitaker, B. I., 2011 National Blood Collection and Utilization Survey. 2011.

3. Janssen, S. J., et al., Allogeneic blood transfusions and postoperative infections after lumbar spine surgery. Spine J, 2015. 15(5): p. 901-9.

4. Blood Preparation Market size worth over USD 64 billion by 2024: Global Market Insights Inc. Oct. 11, 2016; Available from: globenewswire.com/news-release/2016/10/11/878475/0/en/Blood-Preparation-Marketsize-worth-over-USD-64-billion-by-2024-Global-Market-Insights-Inc.html.

5. Bailey, T. L., et al., Protective effects of osmolytes in cryopreserving adherent neuroblastoma (Neuro-2a) cells. Cryobiology, 2015. 71(3): p. 472-80.

6. Li, S., et al., Late embryogenesis abundant proteins protect human hepatoma cells during acute desiccation. Proc Natl Acad Sci USA, 2012. 109(51): p. 20859-64.

7. Solocinski, J., et al., Effect of trehalose as an additive to dimethyl sulfoxide solutions on ice formation, cellular viability, and metabolism. Cryobiology, 2017.

8. Stokich, B., et al., Cryopreservation of hepatocyte (HepG2) cell monolayers: impact of trehalose. Cryobiology, 2014. 69(2): p. 281-90.

9. Zhou, X., et al., Loading trehalose into red blood cells by electroporation and its application in freeze-drying. Cryo Letters, 2010. 31(2): p. 147-56.

10. Satpathy, G. R., et al., Loading red blood cells with trehalose: a step towards biostabilization. Cryobiology, 2004. 49(2): p. 123-36.

11. Slonim, R. W., C.; Garbarino, E., *The Market for Blood*. Journal of Economic Perspectives, 2014. 28(2): p. 177-196.

12. Whitaker, B. I., et al., 2009 National Blood Collection and Utilization Survey2009.

13. Global Blood Processing Devices and Consumables Market, By Product Type (Devices, Consumables), and By Geography—Trends, Size, and Forecast from 2016 to 2024. January 2017; Available from: coherentmarketinsights.com/market-insight/blood-processing-devices-and-consumables-market-83.

14. Scoffin, K. *Instant blood*. Dec. 9, 2012; Available from: soci.org/chemistry-and-industry/cnidata/2012/9/instant-blood.

15. HHS funds development of freeze-dried platelets for disaster response. Sep. 20, 2013; Available from: phe.gov/Preparedness/mcm/Pages/platelets-1309. aspx.

16. Fitzpatrick, G. M., et al., Thrombosomes: a platelet-derived hemostatic agent for control of noncompressible hemorrhage. Transfusion, 2013. 53 Suppl 1: p. 100S-106S.

17. Fitzpatrick, M., 080 Freeze-dried platelets: Advancing towards clinical use. Cryobiology, 2013. 67(3): p. 420.

18. Moradi, S., et al., Artificial Blood Substitutes: First Steps on the Long Route to Clinical Utility. Clin Med Insights Blood Disord, 2016. 9: p. 33-41.

19. Chen, J. Y., et al., A review of blood substitutes: examining the history, clinical trial results, and ethics of hemoglobin-based oxygen carriers. Clinics (Sao Paulo), 2009. 64(8): p. 803-13.

20. Kim, H. O., In-vitro stem cell derived red blood cells for transfusion: are we there yet? Yonsei Med J, 2014. 55(2): p. 304-9.

21. Kanias, T. and J. P. Acker, Trehalose loading into red blood cells is accompanied with hemoglobin oxidation and membrane lipid peroxidation. Cryobiology, 2009. 58(2): p. 232-9.

22. Straat, M., et al., Accelerated clearance of human red blood cells in a rat transfusion model. Intensive Care Med Exp, 2015. 3(1): p. 27.

23. U.S. Pat. No. 5,242,792, filed 1991-02-25, by U.S. Navy, and entitled "Method for the preservation of red blood cells by lyophilization using glycerol or inositol with disaccharides"

24. International Patent Application Publication No. WO 1995/033488, filed 1995-06-02, by Quadrant Holdings, Cambridge Limited, and entitled "Method of preventing aggregation of various substances upon rehydration or thawing and compositions obtained thereby."

25. International Patent Application Publication No. WO 1999/060849, filed 1999-05-26, by Lifecell Corporation, and entitled "Cryopreservation of human red blood cells."

26. International Patent Application Publication No. WO 2001/058431, filed 2000-08-09, by Gendel Limited, and entitled "Method for loading a red blood cell with an agent."

27. International Patent Application Publication No. WO 2004/011616, filed 2003-07-28, by General Hospital Corp., and entitled "Systems and methods for cell preservation."

28. U.S. Patent Application Publication No. US 2006/0188867, filed 2006-01-27, by Canadian Blood Services, and entitled "Method of cryopreserving cells and tissues by liposomal delivery of sugars to enhance post-thaw viability."

29. International Patent Application Publication No. WO 2007/028984, filed 2006-09-07, by University of Dundee, and entitled "Apparatus and method for sonoporation."

30. U.S. Patent Application Publication No. US 2011/0027861, filed 2010-06-04, by Hememics Biotechnologies, and entitled "Desiccated Biologics And Methods Of Preparing The Same."

31. U.S. Patent Application Publication No. US 2014/0073027, filed 2012-06-20, by University of St. Andrews, and entitled "Microfluidic photoporation."

32. International Patent Application Publication No. WO 2015/047502, filed 2014-06-27, by Duke University, and entitled "Systems, apparatus, and methods for droplet-based microfluidics cell poration."

It will be understood that various details of the presently disclosed subject matter can be changed without departing from the scope of the subject matter disclosed herein. Furthermore, the foregoing description is for the purpose of illustration only, and not for the purpose of limitation.

We claim:

1. A method of using sonication to deliver soluble molecules into a plurality of untreated cells to produce treated cells, the method comprising:
   forming a solution comprising an amount of naked positively charged lipid coated microbubbles, an amount of soluble molecules, and a plurality of untreated cells;
   providing a microfluidic device comprising at least a first channel;
   providing an ultrasound device capable of emitting ultrasound waves;
   positioning at least a portion of the first channel in proximity to the ultrasound device;
   passing the solution through the first channel at a sustained predetermined flow rate;
   as the solution passes through the portion of the first channel positioned in proximity to the ultrasound device at the predetermined flow rate, sonoporating a membrane of at least one of the plurality of untreated cells by emitting ultrasound waves from the ultrasound device for a period of time sufficient for the naked positively charged lipid coated microbubbles in the solution to cause a microjetting effect within the fluid surrounding the plurality of untreated cells, forming transient pores in the membrane of at least one of the plurality of untreated cells; and
   wherein the microjetting effect within the solution is sufficient to cause at least a portion of the amount of soluble molecules in the solution to be delivered through the porous membrane of the at least one untreated cell to form at least one treated cell, and wherein the plurality of untreated cells are red blood cells.

2. The method of claim 1, wherein the soluble molecules are selected from the group consisting of trehalose, sucrose, sorbitol, xylitol, myo-iositol, diglycerol phosphate, proline, ectoine, taurine, hypotaurine, and transgenic expressed group 1, group 2, and group 3 Late Embryogenesis Abundant (LEA) proteins from the brine *Artemia franciscana.*

3. The method of claim 1, further comprising a step of drying and/or freezing the at least one treated cells.

4. A method of using sonication to preserve a plurality of red blood cells, the method comprising:
   forming a solution comprising an amount of naked positively charged lipid coated microbubbles, an amount of preservation agent, and a plurality of unpreserved red blood cells;
   providing a microfluidic device comprising at least a first channel;
   providing an ultrasound device capable of emitting ultrasound waves;
   positioning at least a portion of the first channel in proximity to the ultrasound device;
   passing the solution through the first channel at a sustained predetermined flow rate;
   as the solution passes through the portion of the first channel positioned in proximity to the ultrasound device at the predetermined flow rate, sonoporating a membrane of at least one of the plurality of unpreserved red blood cells by emitting ultrasound waves from the ultrasound device for a period of time sufficient for the naked positively charged lipid coated microbubbles in the solution to cause a microjetting effect within the fluid surrounding the plurality of unpreserved red blood cells, forming transient pores in the membrane of at least one of the plurality of unpreserved red blood cells; and
   wherein the microjetting effect within the solution is sufficient to cause at least a portion of the amount of preservation agent in the solution to be delivered through the porous membrane of the at least one unpreserved red blood cell to form at least one preserved red blood cell.

5. The method of claim 4, wherein the preservation agent is selected from the group consisting of trehalose, sucrose, sorbitol, xylitol, myoiositol, diglycerol phosphate, proline, ectoine, taurine, hypotaurine, and transgenic expressed group 1, group 2, and group 3 Late Embryogenesis Abundant (LEA) proteins from the brine *Artemia franciscana.*

6. The method of claim 4, further comprising a step of drying and/or freezing the plurality of preserved red blood cells.

7. A method of using sonoporation to deliver soluble molecules into untreated cells, the method comprising:

passing a solution comprising an amount of naked positively charged lipid coated microbubbles, an amount of soluble molecules, and one or more untreated cells through a microchannel having a shape that causes centrifugal force to be applied to the solution;

providing an ultrasound device capable of emitting ultrasound waves;

positioning at least a portion of the microchannel in proximity to the ultrasound device;

passing the solution through the microchannel at a sustained predetermined flow rate;

as the solution passes through the portion of the microchannel positioned in proximity to the ultrasound device at the predetermined flow rate, sonoporating a membrane of at least one of the untreated cells by emitting ultrasound waves from the ultrasound device for a period of time sufficient for the naked positively charged lipid coated microbubbles in the solution to cause a microjetting effect within the fluid surrounding the one or more untreated cells, forming transient pores in the membrane of at least one of the untreated cells; and wherein the microjetting effect within the solution is sufficient to cause at least a portion of the amount of soluble molecules in the solution to be delivered through the porous membrane of the at least one untreated cell to form at least one treated cell, and wherein the one or more untreated cells are red blood cells.

8. The method of claim 7, wherein the soluble molecules are selected from the group consisting of trehalose, sucrose, sorbitol, xylitol, myo-iositol, diglycerol phosphate, proline, ectoine, taurine, hypotaurine, and transgenic expressed group 1, group 2, and group 3 Late Embryogenesis Abundant (LEA) proteins from the brine *Artemia franciscana*.

9. The method of claim 7, further comprising a steps of separating the one or more treated cells from the solution and drying and/or freezing the one or more treated cells.

10. The method of claim 4, wherein the method further includes the step of applying centrifugal force to the solution as it passes the waves emitted from the ultrasound device.

11. The method of claim 10, further comprising a step of separating the one or more treated cells from the solution and drying and/or freezing the one or more treated cells.

12. The method of claim 1, wherein the ultrasound device comprises a transducer positioned about, above, or below the portion of the first channel in proximity to the ultrasound device.

13. The method of claim 1, wherein the solution is formed by flowing the amount of naked positively charged lipid coated microbubbles, soluble molecules, and plurality untreated cells through the microfluidic device, wherein before combined, the first channel of the microfluidic device contains the amount of microbubbles; a second channel of the microfluidic device contains the amount of soluble molecules, and optionally, the plurality of untreated cells; and wherein the second channel in fluid communication with the first channel.

14. The method of claim 13, wherein the microfluidic device further comprises a third channel for housing the plurality of untreated cells, and wherein the third channel is in fluid communication with the second channel.

15. The method of claim 14, wherein the portion of the first channel in proximity to the ultrasound device is in a spiral configuration.

* * * * *